United States Patent [19]

Agui et al.

[11] 4,216,333
[45] Aug. 5, 1980

[54] PROCESS FOR PREPARING N-TRITYLIMIDAZOLE COMPOUNDS

[75] Inventors: Hideo Agui, Toyonaka; Ikutaro Saji, Osaka; Mitsuo Nakashita, Kobe, all of Japan

[73] Assignee: Sumitomo Chemical Company, Limited, Osaka, Japan

[21] Appl. No.: 7,843

[22] Filed: Jan. 30, 1979

[30] Foreign Application Priority Data

Oct. 30, 1978 [JP] Japan .................................. 53-134178
Oct. 31, 1978 [JP] Japan .................................. 53-134964

[51] Int. Cl.² ........................................... C07D 233/62
[52] U.S. Cl. .................................................. 548/345
[58] Field of Search ........................................ 548/345

[56] References Cited

U.S. PATENT DOCUMENTS

| 3,711,497 | 1/1973 | Buchel | 548/345 |
| 3,767,668 | 10/1973 | Buchel et al. | 548/345 |
| 3,872,095 | 3/1975 | Buchel et al. | 548/345 |
| 3,897,438 | 7/1975 | Draber et al. | 548/345 |
| 3,929,820 | 12/1975 | Buchel | 548/345 |

FOREIGN PATENT DOCUMENTS 47-20015 of 1972 Japan .

Primary Examiner—Alan L. Rotman
Assistant Examiner—Natalie Harkaway
Attorney, Agent, or Firm—Birch, Stewart, Kolasch & Birch

[57] ABSTRACT

A process for preparing N-tritylimidazole compounds of the formula:

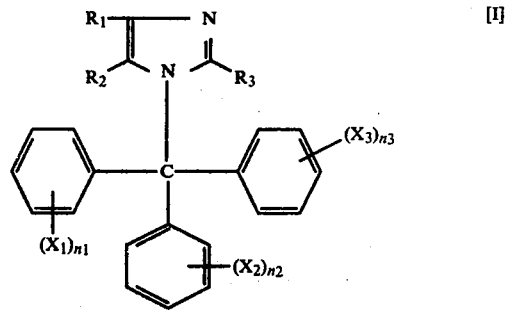

by the reaction between a tritylcarbinol derivative of the formula:

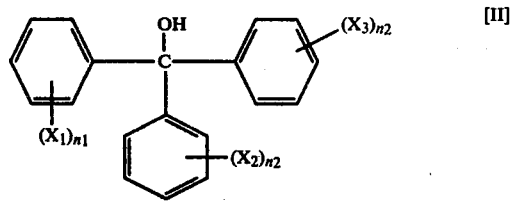

and an imidazole derivative of the formula:

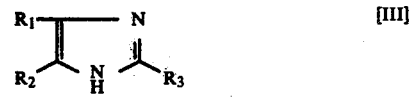

, characterized in that the reaction is effected in the presence of a phosphorus compound of the formula:

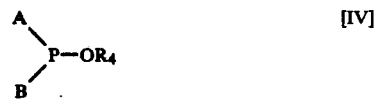

2 Claims, No Drawings

PROCESS FOR PREPARING N-TRITYLIMIDAZOLE COMPOUNDS

The present invention relates to a novel process for producing N-tritylimidazole compounds. More particularly, the invention pertains to an improved process for preparing N-tritylmidazole compounds of the formula:

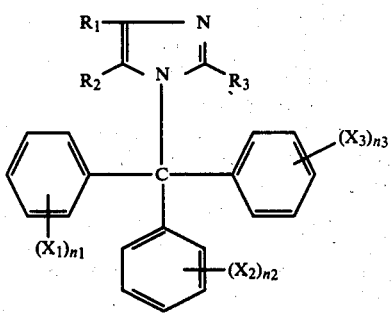

wherein $R_1$, $R_2$ and $R_3$ are independently a hydrogen atom, an alkyl group or a phenyl group, $X_1$, $X_2$ and $X_3$ are independently an alkyl group or an electro-negative moiety and $n_1$, $n_2$ and $n_3$ are each an integer of 0, 1 or 2.

The N-tritylimidazole compounds of the formula [I] are already known to be useful as antimycotic or antibacterial agents [U.S. Pat. Nos. 3,321,366 and 3,705,172].

As disclosed in said U.S. patents, the N-tritylimidazole compounds may be prepared by reacting halides or salts of tritylcarbinol derivatives with silver or sodium salts of imidazole derivatives. However, this method has certain disadvantages. For example, the halides and salts of tritylcarbinol derivatives are unstable in water and hence, difficult to prepare; the silver salts of imidazole derivatives are expensive and unstable upon exposure to light; and, moreover, the yield of the objective compounds is low.

The N-tritylimidazole compounds may also be prepared by reacting tritylcarbinol derivatives with imidazole derivatives. Unlike the aforesaid known method, expensive or unstable starting materials are not required in this process, but the reaction must be carried out at a very high temperature for a long period of time to obtain the objective compounds even in low yields since it does not proceed under ordinary conditions. Thus, this process is also unsatisfactory for commercial production of the N-tritylimidazole compounds.

In order to provide a more convenient and economical process for the production of the N-tritylimidazole compounds, an extensive study has been made, and it has now been found that the reaction of tritylcarbinol derivatives with imidazole derivatives proceeds smoothly under mild conditions to give the N-tritylimidazole compounds in high yields when it is conducted in the presence of a certain phosphorus compound. It has also been found that o-chlorophenyldiphenylmethanol, which is used as the starting material for production of the very potent antifungal compound known as "Clotrimazole" in the process of the invention, can be obtained in a high yield by treating with water the reaction mixture obtained by the Friedel-Crafts reaction of o-chlorobenzotrichloride with benzene in the presence of aluminum chloride.

Thus, the present invention provides a process for preparing the N-tritylimidazole compounds of the formula [I], which comprises reacting a tritylcarbinol derivative of the formula:

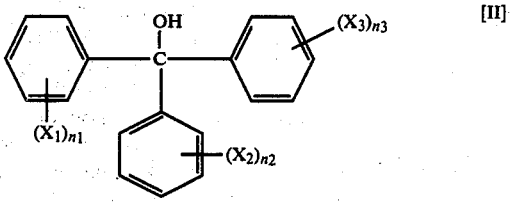

wherein $X_1$, $X_2$, $X_3$, $n_1$, $n_2$ and $n_3$ are each as defined above, with an imidazole derivative of the formula:

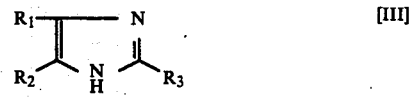

wherein $R_1$, $R_2$ and $R_3$ are each as defined above, in the presence of a phosphorus compound of the formula:

wherein A and B are each an alkyl group, an alkoxy group, an aryl group, an aryloxy group or a hydroxyl group and $R_4$ is an alkyl group or an aryl group.

In a preferred aspect, the invention provides a process for preparing 1-[(2-chlorophenyl)diphenylmethyl]-imidazole which comprises treating the reaction mixture, which is obtained by the reaction of o-chlorobenzotrichloride with benzene in the presence of aluminum chloride, with water to give o-chlorophenyldiphenylmethanol and then reacting o-chlorophenyldiphenylmethanol with imidazole in the presence of the phosphorus compound of the formula [IV].

In the foregoing and, where appropriate, in the subsequent descriptions, the alkyl group for $R_1$, $R_2$, $R_3$, $X_1$, $X_2$ and $X_3$ may be a straight or branched chain alkyl group having one to twelve carbon atoms, preferably having one to four carbon atoms. Examples of preferred alkyl groups are methyl, ethyl, n-propyl, isopropyl, n-butyl, isobutyl, secondary butyl, etc. As the electro-negative moiety, there may be exemplified halogen (e.g. fluorine, chlorine, bromine, iodine), nitro, trifluoromethyl, cyano, alkylthio and alkoxy. As alkylthio and alkoxy, those having one to four carbon atoms are preferred. As used with respect to the formula [IV], aryl and aryloxy may preferably include phenyl and phenoxy, respectively, and alkyl and alkoxy preferably include those having one to four carbon atoms.

In the process of the invention, the N-tritylimidazole compound of the formula [I] is prepared by reacting the tritylcarbinol derivative of the formula [II] with the imidazole derivative of the formula [III] in the presence of the phosphorus compound of the formula [IV], usually at a temperature ranging from about 10° to 130° C., preferably from about 60° to 120° C. in a suitable solvent. In conducting the reaction, the amount of the imidazole derivative [III] is not particularly limited, but good results are obtained when 1 to 3 moles of the imidazole derivative [III] per 1 mole of the tritylcarbinol derivative [II] is used. The amount of the phosphorus compound [IV] may be about 0.5 to 3 moles per 1 mole of the imidazole derivative [III].

As the phosphorus compound [IV], there may be exemplified aryl phosphites such as triphenyl phosphite [P(OC$_6$H$_5$)$_3$] or diphenyl phosphite [H(O)P(OC$_6$H$_5$)$_2$]; an aryl alkylphosphonite such as diphenyl ethylphosphonite; an aryl arylphosphonite such as diphenyl phenylphosphonite [C$_6$H$_5$P(OC$_6$H$_5$)$_2$]; an aryl alkylphosphinite such as phenyl diethylphosphinite [(C$_2$H$_5$)$_2$POC$_6$H$_5$]; an aryl arylphosphinite such as phenyl diphenylphosphinite [(C$_6$H$_5$)$_2$POC$_6$H$_5$]; alkyl phosphites such as triethyl phosphite or trimethyl phosphite; an alkyl arylphosphonite such as diethyl phenylphosphonite; an alkyl alkylphosphonite such as diethyl ethylphosphonite; an alkyl arylphosphinite such as ethyl diphenylphosphinite; and an alkyl alkylphosphinite such as ethyl diethylphosphinite. Among these phosphorus compounds, aryl esters are more effective than alkyl esters in accelerating the reaction, and aryl phosphites such as triphenyl phosphite or diphenyl phosphite are particularly preferred.

The phosphorus compounds of the formula [IV] wherein B is a hydroxyl group are tautomeric. Such tautomers are within the scope of the present invention and are characterized by the formula:

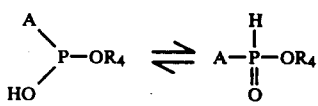

wherein A and R$_4$ are each as defined above.

As the solvents used in the process of the invention, there may be exemplified aromatic hydrocarbons such as benzene or toluene, halogenated aliphatic hydrocarbons such as chloroform or dichloromethane, tetrahydrofuran, methyl isobutyl ketone, dimethylformamide, pyridine, acetonitrile and mixtures thereof.

The tritylcarbinol derivatives of the formula [II] and the imidazole derivatives of the formula [III] are already known and can be prepared by known methods.

In the present invention, Clotorimazole, 1-[(2-chlorophenyl)diphenylmethyl]imidazole, can be prepared by subjecting o-chlorobenzotrichloride with benzene and aluminum chloride to the Friedel-Crafts reaction, then treating the resulting reaction mixture with water to give o-chlorophenyldiphenylmethanol and reacting o-chlorophenyldiphenylmethanol with imidazole in the presence of the phosphorus compound of the formula [IV].

The Friedel-Crafts reaction of o-chlorophenyltrichloride with benzene may be carried out in a conventional way [Arzneim. Forsch., 22 (8), 1260 (1972)]. For example, it can preferably be carried out by reacting 1 mole of o-chlorobenzotrichloride with 1.1 to 2 moles of aluminum chloride in benzene at a temperature ranging from about 40° to 80° C., preferably from about 60° to 80° C. The amount of benzene used in this reaction may vary with the amount of aluminum chloride and the volume of the reaction vessel, but it is convenient to use 3 to 8 times as much benzene as the weight of aluminum chloride used. o-Chlorophenyldiphenylmethanol can be prepared by treating the reaction mixture obtained as above with water at a temperature ranging from 50° C. to the reflux temperature of the reaction system. The amount of water used in this process is not particularly limited, but the process can conveniently be operated when the quantity of water employed is at least 5 times as much as the weight of aluminum chloride used.

The following examples are given to illustrate the present invention more precisely, but it is not intended to limit the present invention thereto.

EXAMPLE 1

(A) Preparation of o-chlorophenyldiphenylmethanol

Into a flask, benzene (380 ml) was charged, and aluminum chloride (88 g) was suspended therein. A solution of o-chlorobenzotrichloride (138 g, 0.6 mole) in benzene (145 ml) was dropwise added thereto over 2 hours while keeping the temperature at 60° C. After the addition was completed, the mixture was refluxed for 2 hours. The reaction mixture was poured into water (600 ml), and the flask was washed with benzene (240 ml) and water (120 ml). The combined mixture was refluxed for 4 hours. The organic layer was separated, washed with water (400 ml), treated with charcoal (6 g) and filtered. Evaporation of the benzene filtrate gave 172.6 g of o-chlorophenyldiphenylmethanol as a crystalline mass. Yield, 97.7%. M.P., 88.5°–91.5° C.

(B) Purification of o-chlorophenyldiphenylmethanol

Eighty grams of o-chlorophenyldiphenylmethanol (M.P., 88.5°–91.5° C.) obtained in (A) was recrystallized from isopropanol to give 71 g of the pure compound having a melting point of 92°–94° C.

Elementary analysis: Calcd. for C$_{19}$H$_{15}$OCl: C, 77.41%; H, 5.13%; C, 12.03%. Found: C, 77.58%; H, 5.01%; Cl, 12.30%.

(C) Preparation of 1-(o-chlorophenyldiphenylmethyl)imidazole

A mixture of pyridine (15 ml), diphenyl phosphite (2.34 g), imidazole (0.68 g) and o-chlorophenyldiphenylmethanol (2.36 g) obtained in (A) was refluxed for 3 hours. Pyridine was removed under reduced pressure, and the residue was extracted with dichloromethane. The extract was washed with a 5% aqueous sodium hydroxide solution and water in order, dried over magnesium sulfate and evaporated to give 1.98 g of 1-(o-chlorophenyldiphenylmethyl)imidazole. Yield, 71.8%. Recrystallization from acetonitrile gave colorless prisms. M.P., 142°–143° C.

Elementary analysis: Calcd. for C$_{22}$H$_{17}$N$_2$Cl: C, 76.63%; H, 4.97%; N, 8.12%. Found: C, 76.38%; H, 5.11%; N, 7.95%.

EXAMPLE 2

Preparation of 1-(o-chlorophenyldiphenylmethyl)imidazole

A mixture of benzene (20 ml), diphenyl phosphite (5.62 g, 24 mmole), imidazole (2.45 g, 36 mmole) and o-chlorophenyldiphenylmethanol (2.95 g, 10 mmole) obtained in Example 1 (A) was refluxed for 8 hours. After cooling, the reaction mixture was washed with a 5% aqueous potassium hydroxide solution (20 ml). The benzene layer was separated, washed with water, dried over magnesium sulfate and evaporated. Recrystallization of the crystalline residue from acetonitrile gave 2.51 g of 1-(o-chlorophenyldiphenylmethyl)imidazole. Yield, 73%. M.P., 142°–143° C.

EXAMPLE 3

Preparation of 1-(o-chlorophenyldiphenylmethyl)imidazole

A mixture of toluene (20 ml), diphenyl phosphite (2.07 g, 6.7 mmole), imidazole (1.09 g, 16 mmole) and o-chlorophenyldiphenylmethanol (2.95 g, 10 mmole) obtained in Example 1 (A) was refluxed for 4 hours. After cooling to room temperature, the reaction mixture was washed with a 5% aqueous potassium hydroxide solution (20 ml). The toluene layer was separated, washed with water, dried and evaporated to give a crystalline mass. Recrystallization from acetonitrile gave 2.57 g of 1-(o-chlorophenyldiphenylmethyl)imidazole. Yield, 74.5%. M.P., 142°–143° C.

EXAMPLE 4

Preparation of 1-(o-chlorophenyldiphenylmethyl)imidazole

A mixture of methyl isobutyl ketone (150 ml), diphenyl phosphite (32.8 g), imidazole (13.6 g) and o-chlorophenyldiphenylmethanol (29.5 g) obtained in Example 1 (A) was refluxed for 4 hours. A 10% aqueous sodium hydroxide solution (250 ml) was added thereto and the resultant mixture was refluxed for 1 hour. After cooling to room temperature, the organic layer was separated, washed with water, and evaporated to give a crystalline mass. Recrystallization from methyl isobutyl ketone gave 26.5 g of 1-(o-chlorophenyldiphenylmethyl)imidazole. Yield, 77%. M.P., 142°–143° C.

EXAMPLE 5

Preparation of 1-(o-chlorophenyldiphenylmethyl)imidazole

A mixture of methyl isobutyl ketone (150 ml), triphenyl phosphite (24.8 g), imidazole (10.9 g) and o-chlorophenyldiphenylmethanol (29.5 g) obtained in Example 1 (A) was heated at 100° C. for 5 hours. The reaction mixture was treated in the same manner as in Example 4 to give 26.9 g of 1-(o-chlorophenyldiphenylmethyl)imidazole. Yield, 78%. M.P., 143°–144° C.

EXAMPLE 6

Preparation of 1-(o-chlorophenyldiphenylmethyl)imidazole

A mixture of methyl isobutyl ketone (60 ml), diphenyl phosphite (13.1 g), imidazole (5.44 g) and o-chlorophenyldiphenylmethanol (11.78 g) obtained in Example 1 (B) was heated at 85° C. for 4 hours. To the reaction mixture, a 10% aqueous sodium hydroxide solution (110 g) was added, and the mixture was refluxed for 1 hour. After cooling to room temperature, the organic layer was separated, washed with water and concentrated to dryness under reduced pressure to give 13.8 g of 1-(o-chlorophenyldiphenylmethyl)imidazole. Yield, 100%. M.P., 138°–142° C. Recrystallization from methyl isobutyl ketone gave 12.3 g of the pure compound. Yield, 89%. M.P., 142°–143° C.

EXAMPLE 7

Preparation of 1-(o-chlorophenyldiphenylmethyl)imidazole

A mixture of o-chlorophenyldiphenylmethanol (29.5 g) obtained in Example 1 (B), triphenyl phosphite (24.8 g), imidazole (12.3 g) and methyl isobutyl ketone (150 ml) was heated at 100° C. for 5 hours. The reaction mixture was treated in the same manner as in Example 6 to give 30.0 g of 1-(o-chlorophenyldiphenylmethyl)imidazole. Yield, 87%. M.P., 143°–144° C.

EXAMPLE 8

Preparation of 1-(o-chlorophenyldiphenylmethyl)imidazole

A mixture of pyridine (15 ml), diphenyl phosphite (2.34 g), imidazole (0.68 g) and o-chlorophenyldiphenylmethanol (2.36 g) obtained in Example 1 (B) was refluxed for 3 hours. The reaction mixture was treated in the same manner as in Example 1 (C) to give 2.16 g of 1-(o-chlorophenyldiphenylmethyl)imidazole. Yield, 78.3%. M.P., 142°–143° C.

EXAMPLE 9

Preparation of 1-(o-chlorophenyldiphenylmethyl)imidazole

A mixture of benzene (20 ml), diphenyl phosphite (5.62 g, 24 mmole), imidazole (2.45 g, 36 mmole) and o-chlorophenyldiphenylmethanol (2.95 g, 10 mmole) obtained in Example 1 (B) was refluxed for 8 hours. The reaction mixture was treated in the same manner as in Example 2 to give 2.72 g of 1-(o-chlorophenyldiphenylmethyl)imidazole. Yield, 79%. M.P., 143°–144° C.

EXAMPLE 10

Preparation of 1-(o-chlorophenyldiphenylmethyl)imidazole

A mixture of toluene (20 ml), triphenyl phosphite (2.07 g, 6.7 mmole), imidazole (1.09 g, 16 mmole) and o-chlorophenyldiphenylmethanol (2.95 g, 10 mmole) obtained in Example 1 (B) was refluxed for 4 hours. The reaction mixture was treated in the same manner as in Example 3 to give 2.80 g of 1-(o-chlorophenyldiphenylmethyl)imidazole. Yield, 81%. M.P., 142°–143° C.

EXAMPLE 11

Preparation of 1-triphenylmethylimidazole

A mixture of pyridine (15 ml), diphenyl phosphite (2.34 g, 10 mmole), imidazole (0.68 g, 10 mmole) and triphenylmethanol (2.08 g, 8 mmole) was refluxed for 3 hours. Pyridine was removed under reduced pressure, and the residue was extracted with dichloromethane. The extract was washed with a 5% aqueous hydroxide solution and water in order, dried and evaporated. Recrystallization of the residue (2.23 g) from acetonitrile gave 2.05 g of 1-triphenylmethylimidazole as colorless needles. Yield, 82.7%. M.P., 221°–223° C.

Elementary analysis: Calcd. for $C_{22}H_{18}N_2$: C, 85.13%; H, 5.85%; N, 9.03%. Found: C, 85.20%; H, 6.03%; N, 9.21%.

EXAMPLE 12

Preparation of 1-triphenylmethylimidazole

A mixture of pyridine (15 ml), triphenyl phosphite (1.55 g, 5 mmole), imidazole (0.68 g, 10 mmole) and triphenylmethanol (2.08 g, 8 mmole) was refluxed for 3 hours. The reaction mixture was treated in the same manner as in Example 11 to give 2.05 g of 1-triphenylmethylimidazole as colorless needles. Yield, 82.7%. M.P., 218°–221° C.

EXAMPLE 13

Preparation of 1-triphenylmethylimidazole

1-Triphenylmethylimidazole was obtained by using dimethyl phosphite instead of diphenyl phosphite in Example 11.

EXAMPLE 14

Preparation of 1-triphenylmethylimidazole

1-Triphenylmethylimidazole was obtained by using triethyl phosphite instead of diphenyl phosphite in Example 11.

What is claimed is:

1. A process for preparing N-tritylimidazole of the formula:

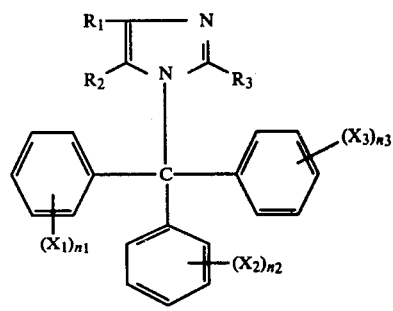

[I]

wherein $R_1$, $R_2$ and $R_3$ are independently hydrogen, alkyl having one to twelve carbon atoms or phenyl, $X_1$, $X_2$ and $X_3$ are independently alkyl having one to twelve carbon atoms, halogen, nitro, trifluoromethyl, cyano, alkylthio having one to four carbon atoms or alkoxy having one to four carbon atoms and $n_1$, $n_2$ and $n_3$ are each zero or an integer of 1 to 2, which process comprises reacting a tritylcarbinol derivative of the formula:

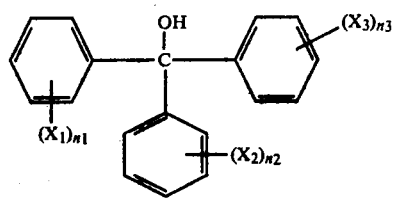

[II]

wherein $X_1$, $X_2$, $X_3$, $n_1$, $n_2$ and $n_3$ are each as defined above, with 1 to 3 moles, per mole of the tritylcarbinol (II), of an imidazole derivative of the formula:

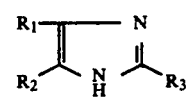

[III]

wherein $R_1$, $R_2$ and $R_3$ are each as defined above, in the presence of a phosphorus compound of the formula:

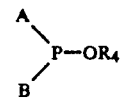

[IV]

wherein A and B are each phenyl, phenoxy, alkyl having one to four carbon atoms, alkoxy having one to four carbon atoms or hydroxy and $R_4$ is phenyl or alkyl having one to four carbon atoms, the amount of said phosphorus compound being in a range of from 0.5 to 3 moles per 1 mole of the imidazole derivative (III) at a temperature ranging from 10° to 130° C. in a suitable solvent.

2. A process according to claim 1, wherein the solvent is a member selected from the group consisting of benzene, toluene, chloroform, dichloromethane, tetrahydrofuran, methyl isobutyl ketone, dimethylformamide, pyridine and acetonitrile, and the phosphorus compound of the formula (IV) is a member selected from the group consisting of triphenyl phosphite, diphenyl phosphite, diphenyl ethylphosphonite, diphenyl phenylphosphonite, phenyl diethylphosphinite, phenyl diphenylphosphinite, triethyl phosphite, trimethyl phosphite, diethyl phenylphosphonite, diethyl ethylphosphonite, ethyl diphenylphosphinite and ethyl diethylphosphinite.

* * * * *